(12) United States Patent
Beech et al.

(10) Patent No.: US 8,075,696 B2
(45) Date of Patent: Dec. 13, 2011

(54) METHOD OF RECOVERING HEAT TRANSFER IN REACTOR AND REGENERATOR EFFLUENT COOLERS

(75) Inventors: James H. Beech, Kingwood, TX (US); Richard E. Walter, Long Valley, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1031 days.

(21) Appl. No.: 11/818,233

(22) Filed: Jun. 13, 2007

(65) Prior Publication Data

US 2010/0018549 A1    Jan. 28, 2010

(51) Int. Cl.
*C23G 1/00* (2006.01)

(52) U.S. Cl. .... 134/2; 134/4; 134/7; 134/10; 134/22.11; 208/161; 585/634; 585/639; 585/640; 585/910; 585/911

(58) Field of Classification Search .................. 134/2, 4, 134/7, 10, 22.11; 208/161; 585/634, 639, 585/640, 910, 911
See application file for complete search history.

(56) References Cited

U.S. PATENT DOCUMENTS

| | | | |
|---|---|---|---|
| 2,908,485 A * | 10/1959 | Longwell | 165/101 |
| 4,750,274 A | 6/1988 | Erdman, Jr. et al. | |
| 5,000,255 A * | 3/1991 | Pflum | 165/104.16 |
| 5,006,304 A | 4/1991 | Franklin et al. | |
| 5,059,331 A | 10/1991 | Goyal | |
| 6,571,420 B1 | 6/2003 | Healy et al. | |
| 6,835,361 B2 | 12/2004 | Yuill et al. | |
| 6,870,072 B2 * | 3/2005 | Lumgair et al. | 585/639 |
| 2005/0201927 A1 | 9/2005 | Flynn et al. | |

OTHER PUBLICATIONS

R. W. Fox et al., "Internal Incompressible Viscous Flow", Introduction to Fluid Mechanics, Fourth ed., (1992), John Wiley & Sons, Inc., Chapter 8, pp. 321-323.

* cited by examiner

*Primary Examiner* — Prem C Singh
(74) *Attorney, Agent, or Firm* — Kevin M. Faulkner; Gerald J. Hughes

(57) ABSTRACT

This invention relates to a method for removing fouling from a heat transfer surface, such as a heat exchanger. The method involves conducting a vapor containing a scouring material to the heat transfer surface and contacting the scouring material with the foulant, the heat transfer surface, or both. Scouring material and removed foulant can be recovered and conducted away.

7 Claims, 3 Drawing Sheets

METHOD OF RECOVERING HEAT TRANSFER IN REACTOR AND REGENERATOR EFFLUENT COOLERS

FIELD OF THE INVENTION

This invention generally relates to a process for decreasing equipment fouling in reactor and/or regenerator effluent streams, such as an effluent stream obtained from an oxygenate to olefins reaction system.

BACKGROUND OF THE INVENTION

Fluidized catalyst conversion processes, such as Fluidized Catalytic Cracking ("FCC") and Oxygenate to Olefins conversion ("OTO"), typically involve contacting a liquid or vapor feed with flowing molecular sieve catalyst particles at elevated temperature. The catalyst is generally separated from the reaction effluent in a disengagement region, where the reaction product is conducted away for further processing while returning the separated catalyst to the process. While a substantial portion of the catalyst particles is separated from the product effluent some portion of the catalyst particles (generally fines) will be conducted away from the process with the effluent vapor. Since carbon deposits form on the molecular sieve catalyst during the desired reaction, all or a portion of the separated catalyst is typically conducted to a regenerating region where the carbon is removed by oxidation, thereby restoring at least a portion of the catalyst's activity. Catalyst continuously returned to the conversion process from the regenerator is conventionally called equilibrium catalyst, or "Ecat". As is the case with reactor product effluent, a substantial portion of the catalyst particles can be separated from the regenerator's vapor effluent ("flue gas"), but a portion of the catalyst particles (generally fines) will generally be conducted away from the regenerator with the flue gas.

For a conventional OTO process carried out in a fluid bed reactor/regenerator system, the fresh and Ecat catalyst particles used in the process typically range in particle size from about 1 to about 200 micrometers. An average particle size is on the order of about 75 micrometers. In operation, catalyst attrition tends to produce catalyst fines, i.e., catalyst particle fragments generally less than 40 micrometers and more typically less than 20 micrometers in size (or average diameter when the fines are spherical or approximately spherical). Even though steps are taken to remove them, a portion of the fines are generally conducted away from the process with either the reactor effluent, the regenerator effluent, or both.

The reactor and regenerator effluent streams are high-temperature streams, and it is frequently desirable to cool these streams during processing using, e.g., conventional heat exchange equipment. The catalyst fines in the effluent can adhere to the heat transfer surfaces in the heat exchange equipment, which lead to heat exchanger fouling resulting in a loss in cooling efficiency. There is therefore a need for a process for removing catalyst fines foulant from the heat transfer surfaces in the reactor and regenerator effluent heat exchangers.

SUMMARY OF THE INVENTION

In an embodiment, the invention relates to a method for removing foulant from a heat-transfer surface, comprising
(a) conducting a vapor stream containing a scouring material (which can also be referred to as a "scouring agent", or "scourant") to the metallic heat-transfer surface (e.g., a surface that has foulant present), the foulant being bound to the heat-transfer surface by at least an electrostatic binding energy; and
(b) contacting the scouring agent with the foulant and/or the heat transfer surface, the scouring agent prior to contact having a kinetic energy greater than the electrostatic binding energy, in order to remove the foulant from the heat transfer surface. The foulant can be and typically is in particulate form for example, the foulant bound to the heat exchange can be in the form of an aggregation of foulant particles.

In another embodiment, the invention relates to a fouling mitigation method in an oxygenate to olefin reaction system, the method comprising:
(a) contacting a feed comprising oxygenate and a catalytically effective amount of an oxygenate conversion catalyst in a reaction zone under catalytic conversion conditions to make a product comprising olefin;
(b) separating a portion of the catalyst from the product;
(c) conducting the product to a heat transfer zone comprising at least one heat transfer surface and depositing at least a portion of the catalyst in the product on the heat transfer surface, the catalyst being bound to the heat transfer surface by a total binding energy comprising an electrostatic binding energy; and
(d) injecting a scouring agent into the product upstream of the heat transfer surface for removing the deposited catalyst wherein the scouring agent has a kinetic energy in proximity to the heat transfer surface greater than the electrostatic binding energy.

In a related embodiment, the method further comprises the steps of
(e) regenerating a portion of the separated catalyst in a regeneration zone in the presence of an oxygen-containing gas to make an effluent comprising regenerated catalyst and a flue gas;
(f) Separating a portion of the regenerated catalyst from the flue gas and conducting the separated regenerated catalyst to the reaction zone and/or the regeneration zone;
(g) conducting the flue gas to a second heat transfer zone comprising at least one heat transfer surface and depositing at least a portion of the regenerated catalyst in the flue gas thereon, the regenerated catalyst being bound to the heat transfer surface of the second heat transfer zone by a second total binding energy comprising a second electrostatic binding energy; and
(h) injecting a second scouring agent into the flue gas upstream of the second heat transfer zone for removing the deposited regenerated catalyst wherein the second scouring agent has a kinetic energy in proximity to the heat transfer surface of the second heat transfer zone greater than the second electrostatic binding energy.

In yet another embodiment, the invention relates to a method for removing particulate from a heat transfer surface, comprising:
(a) conducting a fluid containing a particulate through a heat exchange zone comprising at least one heat transfer surface;
(b) adhering at least a portion of the particulate to the heat transfer surface; and
(c) entraining a scouring agent in the fluid upstream of the heat exchange zone under conditions sufficient to remove at least a portion of the adhered particulate from the heat transfer surface.

In a related embodiment, the foulant is bound to the heat transfer surface by a binding energy comprising an electrostatic binding energy, and wherein the scouring agent has a kinetic energy in proximity to the heat transfer surface greater than the electrostatic binding energy.

In a method related to any of the preceding embodiments, the scouring agent has a kinetic energy in proximity to the heat transfer surface sufficient to overcome all adhesive forces between the foulant and the heat transfer surface.

In a method related to any of the preceding embodiments, the scouring agent is at least one of inorganic oxide, equilibrium catalyst, rock salt, or walnut shells.

In a method related to any of the preceding embodiments, the scouring agent comprises sand.

In a method related to any of the preceding embodiments, the fluid comprises an effluent from a catalytic process for converting a feed comprising oxygenate to a product comprising olefins, a catalyst regeneration process, or both; and wherein at least some of the particulate contains molecular sieve. In a method related to any of the preceding embodiments, the molecular sieve comprises $[AlO_4]$, $[PO_4]$, and $[SiO_4]$ tetrahedral units.

In a method related to any of the preceding embodiments, the heat transfer surface comprises at least one metallic species, and the scouring agent is characterized by a size ranging from 1 to 500 micrometers, a density ranging from 0.5 to 4 $g/cm^3$, an electrical resistivity of $1\times10^{15}$ ohm cm or less, and a velocity of about 90 ft/s to about 200 ft/s in proximity to the heat-transfer surface.

BRIEF DESCRIPTION OF THE DRAWINGS

Examples of the invention are provided with reference to the attached Figures, wherein.

DETAILED DESCRIPTION OF THE INVENTION

Figure 1:
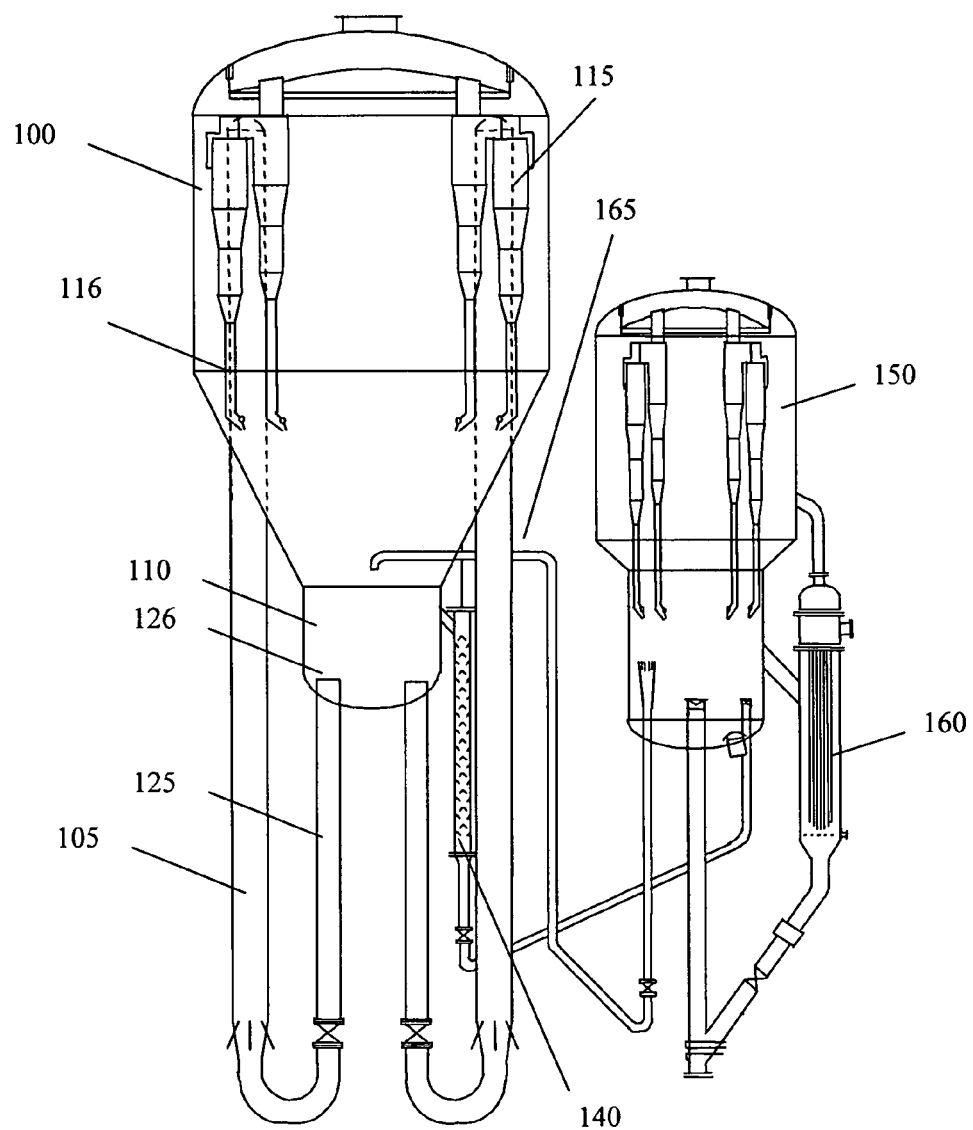
FIG. 1 shows a flow diagram of a representative system for catalytically converting an oxygenate feed to an olefin product.

Molecular sieve catalyst fines are typically present in the effluent from either or both of an OTO reactor and an associated regenerator. Catalyst fines constitute a major portion of the particulates present in the OTO reactor and regenerator effluent.

As a consequence of their relatively high electrical resistivity, the entrained fines have been found to develop an electrical charge which results in the fines adhering to metallic surfaces downstream of the reactor and regenerator. The electrostatic charge on the entrained fines is one component of the total binding energy which causes the fines to adhere to the surface. In addition to the electrostatic binding energy, the total binding energy can optionally comprise other binding energies, such as a visco-elastic binding energy. These effects, alone and in combination, can result in the accumulation of a large amount catalyst fines on the process equipment downstream of the reactor and regenerator, particularly the inside surface (tube side) of heat exchanger tubes. Heat exchangers are typically used downstream of OTO reactors and regenerators for removing heat from the high-temperature effluent streams. Fines accumulation on the tube side of the heat exchanger fouls the inside surface of the tube, resulting in a loss of cooling efficiency. The material accumulating on the tube side of the heat exchanger (fines, heavy hydrocarbon, etc.) is conventionally called "foulant".

The invention is based in part on the discovery that high-resistivity solid materials such as molecular sieve catalyst, which are bound to a metallic surface at least by electromagnetic (generally electrostatic) forces, either alone or in combination with other forces, can be removed under appropriate conditions using a flowing scouring material. The scouring material, which can be inorganic oxide (e.g., sand, etc.), rock salt, walnut shells, and the like, is conducted to the heat exchanger tube in a flowing carrier liquid or vapor, which can comprise and preferably comprises the reactor effluent and/or the regenerator effluent. When the scouring material contacts the heat transfer surface and/or foulant, the foulant is removed from the surface, thereby restoring (or partially restoring) the surface's heat transfer efficiency. To remove the foulant, the scouring material should have a kinetic energy greater than the foulant's electrostatic binding energy, where the term "electrostatic binding energy refers to the energy binding the foulant to the heat transfer surface by electrostatic forces. Optionally, the scouring material should have a kinetic energy greater than the total binding energy of the foulant, where the term "total binding energy" refers to the energy from all forces binding the foulant to the heat transfer surface. In other words, the scouring material is selected so that it contains scouring particles having a sufficient mass so that at the velocity of the carrier fluid the scouring particles have a kinetic energy greater than the electrostatic binding energy (preferably the total binding energy) of the catalyst fines bound to the heat transfer surface. While not required, generally the heat transfer surface is metallic, i.e., it comprises one or more species (including, e.g., oxides) containing at least one metal.

Mass, electrical resistivity, size, density, velocity (in proximity to the heat transfer surface) and kinetic energy (in proximity to the heat transfer surface) ranges for representative scouring materials appear in the Table below. "Size" means average size, e.g., the average diameter when the particles are approximately spherical.

TABLE 1

| Scouring material | Size (diameter in micrometers) | Electrical Resistivity (Ohm cm) | Density (g/cm$^3$) | Velocity (ft/s) | Kinetic energy (joules $\times 10^{-12}$) |
|---|---|---|---|---|---|
| Quartz | 1 to 1000 | $7.5 \times 10^{20}$ | 2.62 | 90 to 200 | 5.6E−09 to 27.4 |
| Fused silica | 1 to 1000 | $5 \times 10^{16}$ | 2.2 | 90 to 200 | 4.7E−09 to 23.0 |
| Silicon Carbide | 1 to 1000 | $10^2\text{-}10^6$ | 3.1 | 90 to 200 | 6.6E−09 to 32.5 |
| Alpha Alumina | 1 to 1000 | $>10^{14}$ | 3.9 | 90 to 200 | 8.3E−09 to 40.8 |
| Gamma alumina | 1 to 1000 | $>10^{14}$ | 3.0-4.0 | 90 to 200 | 7.4E−09 to 36.7 |
| Mullite | 1 to 1000 | $>10^{13}$ | 2.8 | 90 to 200 | 5.9E−09 to 29.3 |

TABLE 1-continued

Figure 3:
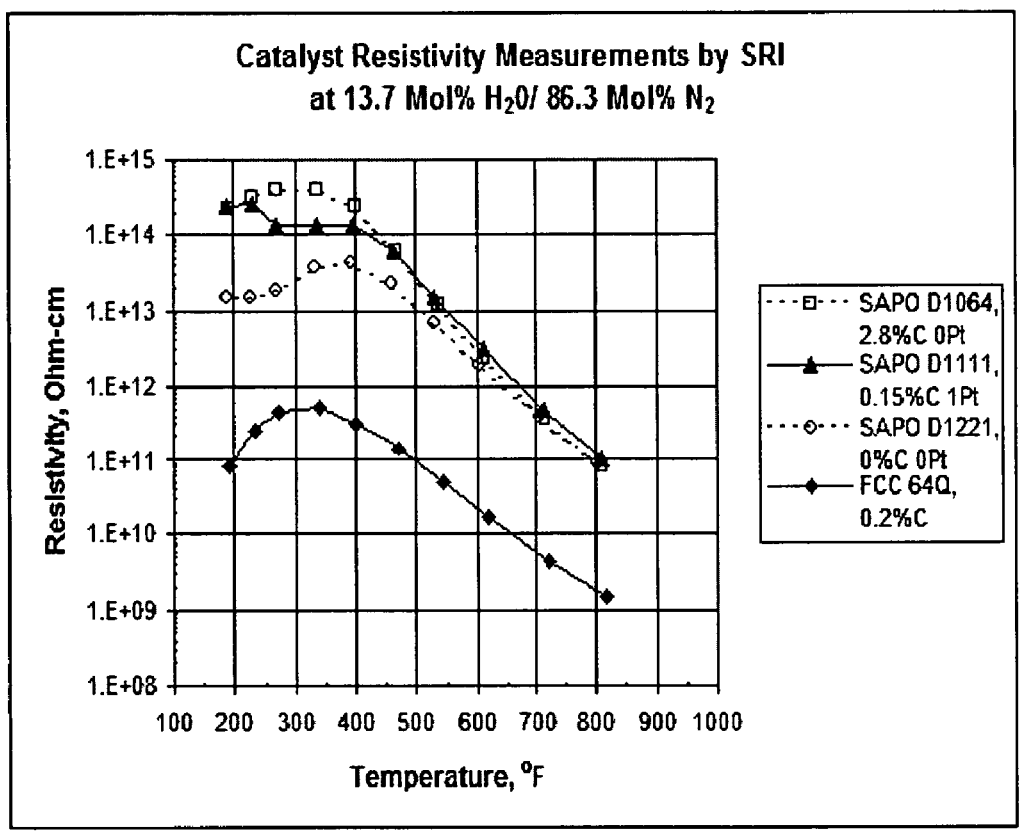
FIG. 3 is a graph comparing the resistivities of certain molecular sieve catalysts.

| Scouring material | Size (diameter in micrometers) | Electrical Resistivity (Ohm cm) | Density (g/cm³) | Velocity (ft/s) | Kinetic energy (joules × $10^{-12}$) |
|---|---|---|---|---|---|
| Zirconium oxide | 1 to 1000 | >$10^{10}$ | 6 | 90 to 200 | 1.3E−08 to 62.8 |
| Boron Nitride | 1 to 1000 | >$10^{14}$ | 1.9 | 90 to 200 | 4.0E−09 to 19.9 |
| FCC Catalyst | 75 to 120 | See Figure 3 | 0.5 to 1.5 (Average bulk density) | 90 to 200 | 1.3E−03 to 2.7E−02 |

For an OTO process, the velocity of the regenerator flue gas generally ranges from about 1 ft/s to about 4 ft/s, and the velocity of the reactor effluent generally ranges from about 10 ft/s to about 60 ft/s. The velocity of the regenerator flue gas in the regenerator heat exchanger generally ranges from about 90 ft/s to about 200 ft/s, and the velocity of the reactor effluent in the reactor effluent heat exchanger also generally ranges from about 90 ft/s to about 200 ft/s. The size (or effective diameter) of the scouring material is not critical provided it has sufficient kinetic energy to dislodge the foulant from the heat transfer surface. In an embodiment, the scouring material is a particulate having an average size that is the same or larger than the foulant. While not required, this is generally the case when the mass density of the scouring material is the same as or less than the mass density of the foulant. In another embodiment, the scouring material has an average size that is the same as or less than the average size of the foulant. While not required, this is generally the case when the mass density of the scouring material is greater than the mass density of the foulant. When the foulant and/or scouring materials are heterogeneous, i.e., when they are not pure substances, then the term "mass density" means average mass density.

In an embodiment, the scouring material has on average a lower electrical resistivity than the catalyst fines, so that the scouring material does not acquire a sufficient charge to cause appreciable adhesion to the heat transfer surface. "Appreciable" in this context means that the scouring material does not adhere to the heat transfer surfaces in an amount great enough to warrant removal to maintain heat transfer efficiency.

When the scouring material has a lower electrical resistivity than the foulant, the electrostatic charge on the scouring particle can be more readily distributed over the entire surface of a scouring material particle than a particle of foulant, and the resulting electrostatic force between the heat transfer surface and the scouring particle is diminished. Consequently, there is less tendency for the scouring material to adhere to the heat transfer surface than for the foulant. Glass (electrical resistivity=$5 \times 10^{16}$ Ohm cm) is an example of a scouring material that has a lower electrical resistivity than the foulant's.

While in one embodiment the electrical resistivity of the scouring material is less than that of the foulant, in another embodiment, the electrical resistivity of the scouring material is the same as or greater than that of the foulant. In this case, in order to lessen the tendency for scouring material to adhere to the heat transfer surface, the size of the scouring material particles can be regulated so that they have a kinetic energy that is at least as large as the electrostatic energy that would otherwise bind the scouring material to the heat transfer surface. Sand (predominantly silica in the form of quartz) having an average electrical resistivity of about $7.5 \times 10^{20}$ ohm-cm is an example of a scouring material having an electrical resistivity greater than the foulant's.

In an embodiment, the scouring material is introduced into the reactor and/or regenerator effluent at a point downstream of the reactor or regenerator vessels. In the embodiment, the scouring material is added to a hopper, such as a conventional blow case. A pressurizing gas, which can be reactor or regenerator effluent gas, then carries the scouring material from the blow case into the effluent stream.

Scouring can be practiced continuously or from time-to-time, depending on the degree of fouling on the heat transfer surface. The scouring material can be removed downstream of the heat exchanger by any method suitable for separating a solid from a vapor stream. Conventional separation equipment such as cyclones, electrostatic precipitators, and the like can be used, alone and in combination. Conveniently, catalyst fines, including those removed as foulant, and other solids can be removed from the heat exchanger effluent with the scouring material.

While not limited to such a process, the invention will be described with reference to an embodiment where the foulant is removed downstream of an OTO reactor, OTO regenerator, or both.

OTO Reaction System

The overall OTO process is carried out in a reaction system. The reaction system includes a reactor (or reactor portion or reactor unit or units), as well as a regenerator (or regenerator portion or regenerator unit or units). The reactor portion can include one or more riser reactor(s), with the reactor(s) terminating at a disengaging section of the reactor portion. In one embodiment, the one or more riser reactor(s) and disengaging section are contained within a single reactor vessel.

OTO Reaction System-Reactor Side

In an embodiment, the OTO process is operated in one or more riser reactors. Generally, fresh or freshly regenerated molecular sieve catalyst particles at elevated temperature are introduced into the riser, and an oxygenate-containing feedstock is then conducted into the riser to contact the catalyst.

The feedstock generally contains one or more oxygenates, i.e., one or more organic compound(s) containing at least one oxygen atom. Preferably, the oxygenate in the feedstock includes one or more alcohol(s), preferably aliphatic alcohol (s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Oxygenates useful in the invention include, for example, methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In a preferred embodiment, the feedstock contains at least one oxygenate selected from the group consisting of methanol, ethanol, dimethyl ether, and diethyl ether; more preferably the oxygenate feed contains methanol and/or dimethyl ether, and most preferably the oxygenate feed contains methanol.

In addition to the oxygenate component, such as methanol, the feedstock may contain one or more diluent(s), which are generally non-reactive with respect to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

Water, when used as a diluent, can be used either in a liquid or a vapor form, or a combination thereof. When a diluent is added to the process, it can be added for example directly to the feedstock entering a reactor, directly to the reactor, or with the molecular sieve catalyst composition.

As the feedstock reacts and flows up through the riser, the catalyst particles become entrained in the feedstock flow. These particles are then removed from the gas-solids flow after exiting the riser typically in a disengagement region.

After the riser effluent, which contains vapor and solids, flows from the riser into the riser termination zone, at least a portion of the solid particles are removed using e.g., separation devices, such as cyclone separators. To increase the efficiency of removal, multiple separation stages can be used.

As the gas-solids flow passes through the separation devices, the flow is separated into a higher density (primarily solids) flow and lower density (primarily gas) flow by each device. For example, in an embodiment where the separation devices are cyclone separator stages, each stage produces a higher density flow that exits the cyclone separator stage through a dipleg. The lower density flow is either passed into the next cyclone separator stage, or after the final stage the lower density flow is passed out of the separation vessel. Because the cyclone separator stages are not perfectly efficient, some product gas will be entrained with the higher density flow as it exits through the dipleg.

Generally, a major amount of solids is separated from the reactor effluent, so that the reactor effluent has an average catalyst loading of greater than or equal to 10 $mg/NM^3$, preferably greater than 20 $mg/NM^3$. In another embodiment, the reactor effluent that exits the reactor vessel has an average catalyst loading of not greater than 200 $mg/NM^3$, preferably not greater than 150 $mg/NM^3$. In another, the reactor effluent has an average catalyst loading of from 10 $mg/NM^3$ to 200 $mg/NM^3$.

After exiting the dipleg, the solid catalyst from the higher density flow (and any entrained product vapor) can be conducted to a transition zone in the separation vessel. The transition zone generally contains a fluidized bed of the catalyst solids. The catalyst bed is the source of catalyst for feeding the risers or standpipes to continue the gas-solids reaction. Optionally, a portion of the catalyst in the transition zone can be conducted to a regeneration zone, as described below.

In the OTO reaction, the feedstock is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene. The amount of olefin(s) produced, based on the total weight of hydrocarbon produced, is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example, greater than 75 weight percent, and preferably greater than 78 weight percent. Typically, the amount of ethylene produced in weight percent based on the total weight of hydrocarbon product produced, is greater than 30 weight percent, such as greater than 35 weight percent, for example, greater than 40 weight percent. In addition, the amount of propylene produced in weight percent based on the total weight of hydrocarbon product produced is greater than 20 weight percent, such as greater than 25 weight percent, for example, greater than 30 weight percent, and preferably greater than 35 weight percent.

The OTO process can be conducted over a wide range of reactor temperatures. For example, average reactor temperatures are in the range of from about 200° C. to about 1000° C. Preferably, the average reactor temperatures are in the range of from about 250° C. to about 800° C.; more preferably from about 250° C. to about 750° C., or from about 300° C. to about 650° C., or from about 350° C. to about 600° C., and most preferably from about 350° C. to about 550° C.

Similarly, the process can be conducted over a wide range of pressures including autogenous pressure. Typically the partial pressure of the oxygenate exclusive of any diluent therein employed in the process is in the range of from about 0.1 kPaa to about 5 MPaa, such as from about 5 kPaa to about 1 MPaa, and preferably from about 20 kPaa to about 500 kPaa.

In a fluidized bed OTO process, the superficial gas velocity (SGV) of the total feedstock, including diluent and reaction products within the reactor system, and particularly within a riser reactor, is generally at least 0.1 meter per second (m/sec), such as greater than 0.5 m/sec. Optionally, the SGV can be greater than 1 m/sec, for example, or greater than 2 m/sec, or greater than 3 m/sec. Typically, the SGV is greater than 4 m/sec. The process can be carried out as a continuous fluidized bed process, e.g., in a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in, for example, U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y., 1977.

Preferred reactor types are riser reactors generally described in *Riser Reactor, Fluidization and Fluid-Particle Systems*, pp. 48 to 59, F. A. Zenz and D. F. Othmo, Reinhold Publishing Corporation, New York, 1960, and U.S. Pat. No. 6,166,282 (fast-fluidized bed reactor). In one practical embodiment, the process is conducted as a fluidized bed process or high velocity fluidized bed process.

OTO Reaction System-Regenerator Side

Catalyst used in an OTO reaction generally accumulates carbon (usually in the form of coke) which leads to a loss in catalytic activity. Consequently, it is generally desirable to conduct all or a portion of the catalyst separated from the reactor effluent to a regeneration zone, or regenerator, for regeneration and re-use. In the regenerator, the coked catalyst is contacted with an effective amount of a regeneration medium, preferably a gas containing oxygen, under catalytic regeneration conditions of temperature, pressure and residence time to burn the carbonaceous material from the catalyst particles and form a flue gas composition.

The catalyst is generally conducted from the reactor vessel (or, optionally from the disengaging zone or transition zone) to the regenerator via standpipes, which generally have a constant diameter throughout. Alternatively, the diameter of the standpipes can vary along the standpipe.

Suitable regeneration media include, e.g., compositions comprising one or more of $O_2$, $O_3$, $SO_3$, $N_2O$, $NO$, $NO_2$, $N_2O_5$ and $H_2O$. For example, the regeneration medium can be one that contains oxygen, air, or oxygen-enriched air. Regeneration conditions are typically conditions capable of burning coke from the coked catalyst, preferably to a level less than 0.5 weight percent, based on the total weight of the catalyst. For example, the regeneration pressure can range from about 15 psia (103 kPaa) to about 500 psia (3,448 kPaa). The residence time of the catalyst composition in the regenerator generally ranges from about one minute to about several hours. Preferably, the coked catalyst is contacted with regeneration medium in the regenerator at an average regenerator temperature of not greater than about 690° C., more preferably not greater than about 660° C., still more preferably not greater than about 630° C.; and most preferably not greater than about 600° C. The temperature as used herein refers to the average temperature measured in the bed of catalyst contained in the regenerator. In other words, regeneration temperature, pressure, and residue time can be conventional, i.e., conditions known to those skilled in the art of OTO conversion.

Since coke burning in the regeneration step is an exothermic reaction, the temperature within the regeneration zone can be controlled e.g., by conducting a cooled gas to the regenerator vessel. Alternatively, a portion of the regenerated catalyst composition can be conducted from the regeneration zone through a catalyst cooler to form a cooled regenerated catalyst which can be conducted back to the reaction or regeneration zone.

In an embodiment, regenerated catalyst composition withdrawn from the regeneration zone, preferably via a catalyst cooler, can be combined with fresh OTO catalyst and/or recirculated OTO catalyst, and then returned to the riser reactor (s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s). In another embodiment, the cooled catalyst is conducted from the catalyst cooler back to the regenerator, and then to the reactor.

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336-337). Coke levels on the catalyst composition can be measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example, from about 0.2 weight percent to about 5 weight percent, and conveniently from about 0.3 weight percent to about 2 weight percent based on the weight of the molecular sieve in the catalyst.

In one embodiment, regenerated catalyst particles are initially separated from the flue gas within the regenerator. Preferably, the regenerated catalyst is separated from the flue gas in a disengaging section or zone of the regenerator, and the separated flue gas stream exits the regenerator.

In one embodiment, a cyclone separation system is used to separate the regenerated catalyst composition from the flue gas that exits the regenerator. Although cyclones are preferred, gravity effects within the disengaging zone can also be used to separate the catalyst composition from the flue gas effluent. Other methods for separating the catalyst composition from the flue gas effluent include the use of plates, caps, elbows, and the like.

The flue gas stream that exits the regenerator can have, for example, an average catalyst loading of greater than or equal to 10 $mg/NM^3$, preferably greater than about 20 $mg/NM^3$. In another embodiment, the flue gas stream that exits the regenerator has an average catalyst loading of not greater than about 200 $mg/NM^3$, preferably not greater than about 150 $mg/NM^3$. In another, the flue gas stream that exits the regenerator has an average catalyst loading of from 10 $mg/NM^3$ to about 200 $mg/NM^3$.

Regenerator Flue Gas and Reactor Effluent

In one embodiment, the catalyst particles are separated from the flue gas stream in the regenerator and from the reactor effluent in the reactor vessel so that the flue gas stream that exits the regenerator and the product effluent that exits from the reactor each have an average catalyst loading of greater than or equal to about 10 $mg/NM^3$. Additional fine catalyst particles can be removed from either the regenerator flue gas stream, the reactor effluent stream, or both by way of a second or subsequent separation step. The dimension "mg/$NM^3$" means milligrams per "normal" cubic meters. The term "normal" refers to a temperature of 0° C. and a pressure of 1.013 bar, the conditions at which one mole of an ideal gas has a volume of 22.413837 liters.

The flue gas stream conducted away from the regenerator, the product effluent stream conducted away from the reactor vessel, or both can contain, e.g., catalyst particles having a $d_{90}$ in a range of from about 20 microns to about 100 microns (micrometers), preferably in a range of from about 30 microns to about 80 microns, and more preferably in a range of from about 40 microns to about 60 microns. As used herein, $d_{90}$ is the average diameter in which the cumulative amount of the sample reaches 90% of the total.

When a fines separation zone is used downstream of the reactor, regenerator, or both, the final flue gas and/or product effluent streams have a $d_{90}$ in a range of from about 0.5 microns to about 15 microns, preferably from about 1 micron to about 10 microns, more preferably from about 1.5 microns to about 5 microns.

FIG. 1 schematically shows an embodiment of a reaction system suitable for performing the invention. In the embodiment shown in FIG. 1, a plurality of riser reactors 105 are provided for performing a gas-solids reaction. The tops of risers 105 are not shown as they are contained within separation vessel 100 (also called the "reactor"). The exits near the top of each riser are coupled with cyclone separator stages 115. During operation, solids separated out by the cyclone separator stages 115 are conducted out of the diplegs 116 and toward transition zone 110 of separation vessel 100. While not required, a fluidized catalyst bed can form in the bottom region of the transition zone, which feeds catalyst to the standpipe entry locations 126 for the standpipes 125. A portion of the catalyst in the catalyst bed can be diverted to regenerator 150 via the conduit containing catalyst stripper 140. Regenerator 150 is optionally provided with a catalyst cooler 160. Regenerated catalyst can be conducted to the reactor via conduit 165. In the embodiment shown in FIG. 1, regenerated catalyst is returned to the top of the transition zone to join the catalyst exiting the cyclone diplegs. More generally, regenerated catalyst can be distributed at the top of the catalyst bed in the transition zone by distribution means, including conventional catalyst distribution equipment.

Reactor and Regenerator Effluent Processing

Typically, catalyst particles, generally including a majority of fine catalyst particles, are entrained with the olefin product stream exiting the reactor. The product stream exiting the reactor also includes a variety of byproducts, including a significant amount of water. Water can be removed from the olefin product stream by cooling the stream to a temperature below the condensation temperature of the water in the stream. Preferably, the temperature of the product stream is initially cooled in a heat exchanger and then subsequently cooled to a temperature below the condensation temperature of the oxygenate feed for the oxygenate to olefins process. Preferably, the olefin product stream is cooled to form a water stream and to remove catalyst particles entrained in the olefin product.

As discussed, catalyst fines in the reactor effluent can develop an electrostatic charge which causes the fines to adhere to and foul the internal channels of the heat exchanger. This results in a decrease in cooling efficiency. In order to overcome this difficulty, scouring material is introduced into the reactor effluent at a point downstream of the reactor vessel and upstream of the heat exchanger. The scouring material can be in the form of a particulate, and can be removed from the process by the solids separation equipment downstream of the heat exchanger.

In certain embodiments, it is desirable to cool the product stream below the condensation temperature of methanol. A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces the condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated hydrocarbon by-products as well as water.

In one embodiment, the quenching fluid is a recycle stream of the condensed water containing heavy bottoms stream of the quench column. This water containing stream can be cooled, e.g., by a second heat exchanger, and injected back into the quench column. The invention is also applicable to foulant removal in this heat exchanger. It is preferred in this embodiment to not inject cooling medium from an outside source into the quench column, although it may be desirable to do so in other separation equipment down stream of the quench column.

The condensed water stream that exits the quench column will contain a major amount of catalyst particles that enter the quench column along with the scouring material and a portion of olefin product from the reactor. The condensed water stream is then sent to the waste treatment system. Optionally, at least a portion of the condensed water stream is sent to a stripper to remove oxygenate byproducts that can also be found in the water stream. In one embodiment, the stripper is a methanol stripper in which methanol is added to a fractionation column. A vapor stream rich in oxygenate can be recovered from the stripper and recycled back to the oxygenate to olefin reactor. A bottoms or liquid stream that exits the stripper contains a major portion of the catalyst particles and scouring material.

In one embodiment, the liquid stream from either the quench column or stripper is sent to a waste treatment system. Optionally, the waste treatment system separates a solid sludge-like material from a clean water stream having a reduced solid content, and the clean water stream is either disposed or at least a portion recycled back to the reaction or recovery system.

Figure 2:
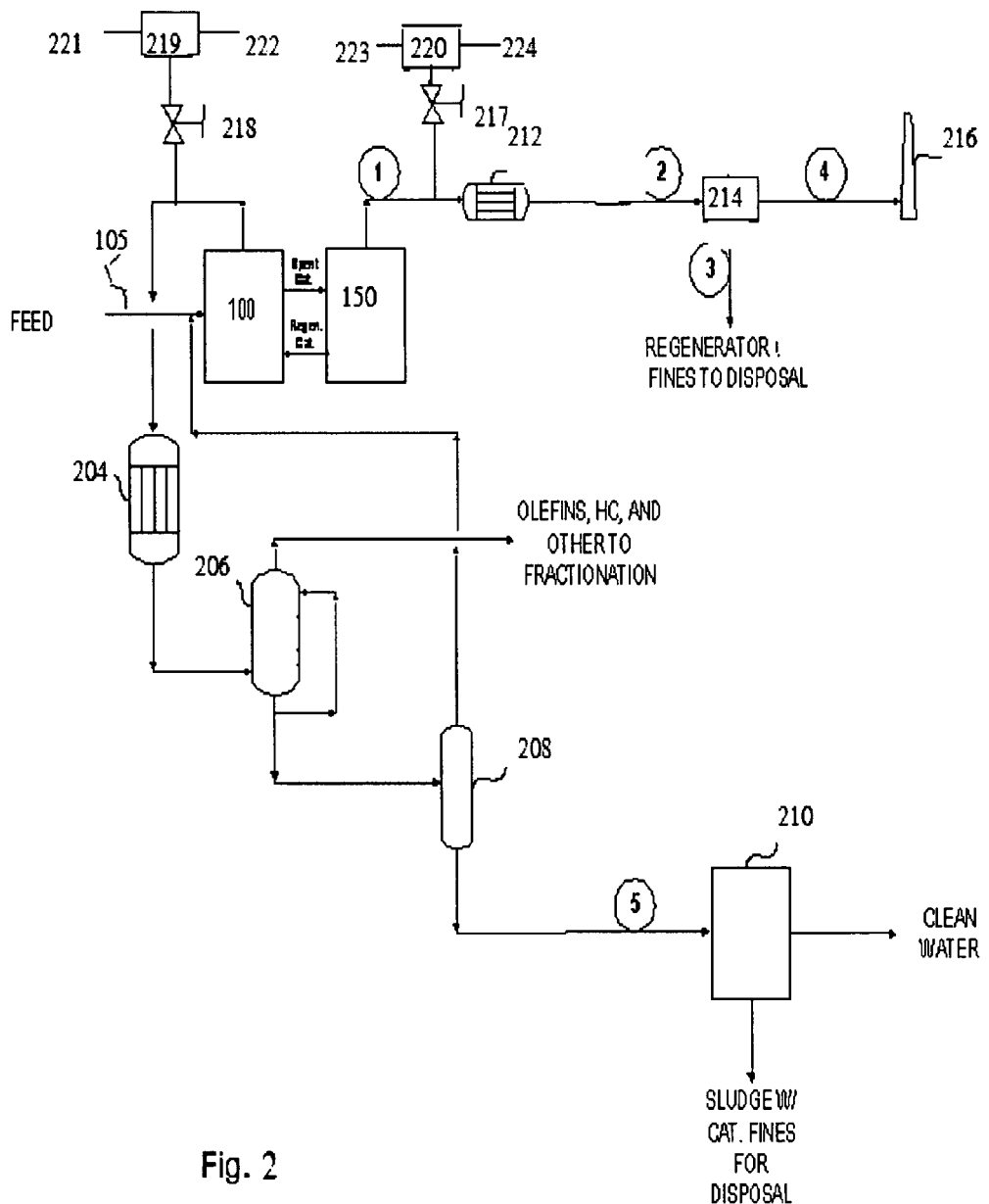
FIG. 2 shows a flow diagram schematically showing the processing of reactor and regenerator effluents.

In an embodiment, the quenched olefin stream is further processed by compression, preferably multi-staged compression. Two, three, four or more stages can be used, with two or three stages being preferred. In another embodiment of the invention, the olefin stream is compressed to a pressure that is greater than that at which the oxygenate to olefin reaction process is carried out. Preferably, the olefin stream is compressed to a pressure of at least about 30 psia (207 kPa), more preferably at least about 50 psia (345 kPa), most preferably at least about 100 psia (689 kPa). High pressure ranges are particularly preferred, with the upper limit being a practical one based on cost of design and ease of operation. Practical high pressure limits are generally considered to be up to about 5,000 psia (34,450 kPa), with lower limits of about 1,000 psia (6,895 kPa), about 750 psia (5,171 kPa), and about 500 psia (3,447 kPa) being increasingly preferred. This compressed stream is then sent to additional recovery processes for separating and recovering different olefin product compositions. Processing of the reactor effluent is shown schematically in FIG. 2.

As shown in the figure, a reaction effluent containing olefin product and a significant amount of water, byproduct, and some catalyst fines, is conducted from vessel 100 to a heat exchanger (effluent cooler) 204, and the cooled product is sent to a quench tower 206. Blow case 219 containing the scouring material is connected to the conduit between the outlet of vessel 100 and heat exchanger 204 by way of control valve 218, which regulates the amount of scouring material introduced into the effluent vapor. Scouring material (also called a scouring agent or scourant) is conducted into the blowcase via line 222. A pressuring gas, introduced via line 221 is used to conduct the scouring material through valve 218 and into the reactor effluent. At the quench tower 206, water is condensed from the olefin and other hydrocarbon vapors. The olefin and hydrocarbon vapors from the quench tower overhead are then conducted away from the process to e.g., product recovery.

A portion of the condensed water stream from quench tower 206 is also recycled, as shown, and preferably further cooled in the recycle. Associated water pumping equipment in the recycle loop is not shown. The condensing of the water and the additional contact of the recycled water stream aid to remove catalyst fines that had been entrained in the olefin product. The condensed water stream includes not only catalyst fines, but also the scouring material and condensable hydrocarbons such as unconverted methanol. This stream is conducted to methanol stripper 208, which separates methanol and lighter hydrocarbons from the water and solids. The methanol and lighter hydrocarbons are recycled back to the process as feed to riser 105, and the water and solids stream 5 is sent to a waste treatment system 210. The waste treatment system preferably includes a solids settler that aids in separating the solid catalyst particles and scouring material from the water. The separated or clean water is then discharged; alternatively, at least a portion can be recycled or reused in the system.

In an embodiment, the scouring material is injected into the regenerator effluent (also called a "flue gas"). This injection can be instead of or in addition to scouring material injection into the reactor effluent. Accordingly, at least a portion of the catalyst in vessel 100 can be conducted to regenerator 150 for coke (carbon) removal. Coke material is removed from the catalyst in the regenerator 150 by burning in the presence of an oxygen containing gas to form the flue gas. The flue gas is separated from the regenerated catalyst in a first separation step within the regenerator, using e.g., a cyclone system. Flue gas containing catalyst fine particles exits the regenerator 150 through a line 1 and is conducted to a heat exchanger (flue gas cooler) 212. As in the case of the reactor-side heat exchanger, this can be a low pressure exchanger that produces low pressure steam, or, alternatively, more that one exchanger can be used to produce low and high pressure steam. Blow case 220 containing the scouring material is connected to the conduit between the outlet of regenerator 150 and heat exchanger 212 by way of control valve 217, which regulates the amount of scouring material introduced into the flue gas. Scouring material is conducted into the blowcase via line 224. A pressuring gas, introduced via line 223 is used to conduct the scouring material through valve 217 and into the flue gas. The flue gas is then cooled by heat exchanger 212. The cooled flue gas containing the catalyst fine particles and scouring agent is then conducted to a solids separation unit 214, for example a high-temperature electrostatic precipitator ("ESP").

The high temperature ESP is operated at high temperature to remove a major amount of the scouring material and catalyst fines from the flue gas, stream 3. A final flue gas composition, stream 4, which is low in particulates, is then sent to a flue gas stack 216 and discharged to the atmosphere. Optional processing to e.g., oxidize carbon monoxide and to remove oxides of nitrogen and sulfur can be provided prior to atmospheric discharge, if needed. These aspects of the process will now be discussed in more detail.

In one embodiment, a second separation step is used to remove additional catalyst particles from flue gas, particularly catalyst fines. In the second step, the flue gas exiting the regenerator is conducted through a catalyst fines separation unit. This unit removes a major amount of catalyst fines to form a final flue gas stream having an average catalyst loading less than that following the first separation step. Preferably, the final flue gas stream has an average catalyst loading that is less than 50 mg/NM$^3$, more preferably less than 10 mg/NM$^3$.

In one embodiment, the catalyst fines separation unit is an ESP, i.e., a system for collecting solid particles, which operates by virtue of the movement of charges immersed in an electric field. When an ESP is used, the flue gas exiting the regenerator is conducted through a zone in which an electric field is directed transversely to the flow. The electric field is operated at a high voltage where a corona of free electrons is emitted from the negative electrode. Preferably, the electrodes charge the catalyst particles flowing in the flue gas through the precipitator, and the charged particles migrate under the effect of the electric field toward the positive electrode. The electrode is preferably designed in the form of collecting plates on which the catalyst particles are deposited. The catalyst particles are electrically discharged at the positive electrodes, and the plates are optionally shaken, so that the collected catalyst particles fall into a hopper located below the plates.

Preferably, the electrostatic precipitator is operated at lower pressures. In one embodiment, the electrostatic precipitator is operated at pressure of not greater than 5 atm. More preferably, the electrostatic precipitator is operated at pressure not greater than 2 atm. Conventional precipitation conditions can be used.

The electrostatic precipitator can be operated over a wide range of temperatures. The temperature range can be affected by the degree of catalyst resistivity or the degree to which the catalyst particles can be ionized. In one embodiment, at relatively high resistivities, for example, greater than $10^{11}$ ohm-cm or greater than $10^{12}$ ohm-cm, preferably greater than $10^{13}$ ohm-cm, it is preferred to operate the electrostatic precipitator at relatively high temperatures. In a particular embodiment, the ESP is operated at a temperature of at least 400° C., preferably at least 450° C.

In another embodiment, the charge on the catalyst particles or the ability of the particle surface to ionize is affected by adding a gas stream to the electrostatic precipitator. Examples of useful gas streams include water, preferably as steam, ammonia, or a combination of water and ammonia.

In one embodiment, wet ESP technology is used. In this embodiment, the ESP is operated at water dew point and with water addition. The addition of the water can be in the form of steam or liquid water or a combination of both. While not wishing to be bound by any theory, it is believed that the water addition lowers the particulate resistivity. It is also believed that the added water wets the catalyst particles on the collector surfaces, reducing entrainment. Consequently, in an embodiment, water addition is conducted at a level that permits the electrostatic plates to be washed, limiting particle buildup. Preferably, the wet ESP is operated at a temperature of not greater than 100° C.

In another embodiment, the catalyst fines separation unit is a filter unit such as a baghouse. The filter unit can be operated at an average temperature of from 100° C. to 450° C., with average temperature being defined as the average of the inlet and outlet temperatures. Optionally, the filter unit can be operated at a temperature below the dew point of the vapor in the filter unit to avoid fouling the filter element, e.g., above 100° C. The filter unit can be operated at a pressure of 5 atm. or less, optimally more preferably not greater than 2 atm. Examples of filter elements that can be used in this invention include, but are not limited to, woven felt, fiberglass, polypropylene, ceramic fiber, Teflon, Nomex or non woven sintered metal or ceramic, and metal or ceramic foams. The melting point of the filter material will define the upper operating temperature of the filter.

In yet another embodiment, the catalyst fines separation unit is a wet gas scrubber that is used to reduce particle load in the flue gas stream. A wet gas scrubber is an apparatus that provides for mass transfer between a liquid and a gas. An exemplary type of scrubber includes a housing that forms a chamber for the mass transfer process. Generally, a conduit or pipe type structure conducts the liquid to the scrubber. This conduit is preferably located on an upper portion of the chamber. The pipe means can include one or more liquid discharge outlets which, in a preferred embodiment, can take the form of sprayers. The sprayers spray the liquid into the top of the scrubber so as to contact the catalyst particles. The liquid is preferably water, and the water can come from any of a variety of sources. The wet gas scrubber acts to remove the catalyst particles so that a flue gas stream low in catalyst loading exits through the outlet.

In a related embodiment, the water stream exiting from the methanol stripper described above is used in the wet gas scrubber to contact the flue gas entering the wet gas scrubber. This stream, as any water stream, can be added to the flue gas stream prior to entering the scrubber or can be added as a separate line directly to the scrubber.

In another embodiment, the water stream exiting the methanol stripper is first sent to a waste water treatment plant for further separation of catalyst particles and water. Preferably, the water stream from the methanol stripper is sent to a clarification unit where solids are separated from the water. The separated water stream from the waste treatment plant or clarification unit is then contacted with the flue gas at the wet gas scrubber to further remove catalyst particles from the flue gas and form the final flue gas stream.

Catalyst Description

In an embodiment, the invention relates to the removal of foulant that comprises fines of a molecular sieve catalyst used in an oxygenated-to-olefin reaction systems, and particularly fines of such catalyst. The catalyst generally contains one or more types of molecular sieve compositions, particularly those types of molecular sieves that contain active catalytic sites that are susceptible to deactivation due to contact with water molecules. In general, molecular sieves have various chemical, physical, and framework characteristics, and have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type zeolite and zeolite-type molecular sieves, for which a structure has been established, are assigned a three letter code and are described in the *Atlas of Zeolite Framework Types,* 5th edition, Elsevier, London, England (2001).

Crystalline molecular sieve materials all have a 3-dimensional, four-connected framework structure of corner-sharing $TO_4$ tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Vol. 137, pp. 1-67, Elsevier Science, B.V., Amsterdam, Netherlands (2001).

In an embodiment, the molecular sieves can be, for example, small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW, and SOD. For example, the molecular sieve can have an AEI topology or a CHA topology, or a combination thereof. The molecular sieves used in this invention can comprise at least one intergrowth phase of AEI and CHA framework-types, e.g., those in which the ratio of CHA framework-type to AEI framework-type, as determined by the DIFFaX method disclosed in U.S. Patent Application Publication No. 2002-0165089, is greater than 1:1.

The small, medium and large pore molecular sieves have from a 4-ring to a 12-ring or greater framework type. Typically, the molecular sieves employed herein have 8-, 10- or 12-ring structures and an average pore size in the range of from about 3 Å to 15 Å. More typically, the molecular sieves used in this invention have 8 rings and an average pore size less than about 5 Å, such as in the range of from 3 Å to about 5 Å, for example, from 3 Å to about 4.5 Å, and particularly from 3.5 Å to about 4.2 Å.

In one embodiment, molecular sieve crystals that are incorporated into the catalyst have a chabazite (CHA) structure, and the crystals are preferably made of a composition having a molar relationship within the structure of:

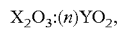

$$X_2O_3:(n)YO_2,$$

wherein X is a trivalent element, such as aluminum, boron, iron, indium, and/or gallium, preferably aluminum; Y is a tetravalent element, such as silicon, tin, titanium and/or germanium, preferably silicon; and n is greater than 10, preferably greater than 50, still more preferably greater than 100, preferably that ranges from about 10 to about 2,000, more preferably from about 50 to about 600, most preferably from about 100 to about 300.

The molecular sieve can be prepared from a reaction mixture containing sources of water, an oxide of a trivalent element X, an oxide of a tetravalent element Y, and an organic templating agent or template. In general, templating agents or templates include compounds that contain elements of Group 15 of the Periodic Table of Elements, particularly nitrogen, phosphorus, arsenic, and antimony. Typical templates also contain at least one alkyl or aryl group, such as an alkyl or aryl group having from 1 to 10 carbon atoms, for example, from 1 to 8 carbon atoms. For example, the templates can be nitrogen-containing compounds, such as amines, quaternary ammonium compounds, and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Such templates include for example tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone. Preferred templates are selected from the group consisting of tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine, heated degraded forms thereof, and combinations thereof. In one embodiment, the template is preferably selected from the group consisting of N-alkyl-3-quinuclidinol, N,N,N-trialkyl-1-adamantammonium cations, N,N,N-trialkyl-exoaminonorbornane and mixtures thereof, and is preferably a N,N,N-tri-methyl-1-adamantammonium cation.

In general, molecular sieve crystals that are incorporated into the catalyst have a molecular framework that includes $[AlO_4]$ and $[SiO_4]$ tetrahedral units. Such molecular sieves include aluminosilicates, particularly those having a chabazite structure.

In another embodiment, molecular sieve crystals that are incorporated into the catalyst have a molecular framework that includes [AlO$_4$], [PO$_4$] and [SiO$_4$] tetrahedral units, such as silicoaluminophosphates (SAPO), and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the catalyst includes silicoaluminophosphate or metal-containing silicoaluminophosphate molecular sieve crystals. Preferably, the SAPO has a Si/Al ratio less than 0.65, such as less than 0.40, for example, less than 0.32, and particularly less than 0.20. In one embodiment, the molecular sieve has a Si/Al ratio in the range of from about 0.65 to about 0.10, such as from about 0.40 to about 0.10, for example, from about 0.32 to about 0.10, and particularly from about 0.32 to about 0.15.

Suitable SAPO molecular sieves include e.g., SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56 and metal containing molecular sieves thereof. Optionally, the molecular sieve is or more of SAPO-18, SAPO-34, SAPO-35, SAPO-44, SAPO-56, and metal containing derivatives thereof. In an embodiment, the molecular sieve is SAPO-34.

In another embodiment, the catalyst incorporates aluminophosphate (AlPO) molecular sieves. These molecular sieves can be included as separate crystals or they can be intermixed with other crystalline structures such as by an intergrowth structure. Examples of aluminophosphates include AlPO-5, AlPO-11, AlPO-18, AlPO-31, AlPO-34, AlPO-36, AlPO-37, and AlPO-46.

In one embodiment, the catalyst includes a combination of at least one SAPO and at least one AlPO molecular sieve, wherein the SAPO and the AlPO and AlPO are selected from those described in the preceding embodiment. For example, the SAPO can be SAPO-18 or SAPO-34, and, the AlPO can be AlPO-34 or AlPO-18.

Additional examples of intergrowth molecular sieves useful in this invention include those described in U.S. Patent Application Publication No. 2002-0165089 and International Publication No. WO 98/15496, published Apr. 16, 1998, the descriptions of those sieves incorporated herein by reference.

In one embodiment, the catalyst particles include a metal oxide and the catalyst particles have a TOF$_{redox}$ of not greater than 1000 sec$^{-1}$, measured at 100° C., preferably not greater than 500 sec$^{-1}$, more preferably not greater than 100 sec$^{-1}$, still more preferably not greater than 10 sec$^{-1}$, and most preferably not greater than 1 sec$^{-1}$. In another embodiment, the catalyst particles include a metal oxide and the catalyst particles have a methoxy decomposition temperature of at least 100° C., preferably at least 200° C., more preferably at least 300° C. The activity for decomposition of the methoxy group and conversion of methanol to oxygenates including dimethyl ether (DME) and carbon dioxide are preferably determined by the method of Badlani, Birand, and Wachs, "Methanol: A 'Smart' Chemical Probe Molecule," presented in the 2001 Spring Symposium of the Catalysis Society of New York Metropolitan, Lehigh University, Lehigh, Pa., March, 2000. Reactivity of methanol conversion is preferably measured by chemisorption of methanol at 100° C. carried out in a thermal gravimetric analyzer (TGA) and subsequent temperature programmed reaction (TPR). The products formed from the TPR are measured using an on-line GC. Formation rate for HCHO, HCOOCH$_3$, and CH$_2$(OCH$_3$)$_2$ is defined as redox activity TOF$_{redox}$ (turnover frequency).

In an embodiment, the catalyst is in the form of fluidizable particles characterized by the following size distribution:

TABLE 2

| Percentage of Catalyst (based on the total mass of catalyst) | Average Particle Size |
|---|---|
| At least 95% | less than 125 micrometers |
| At least 90% | less than 110 micrometers |
| At least 80% | less than 96 micrometers |
| At least 70% | less than 88 micrometers |
| At least 60% | less than 83 micrometers |
| At least 50% | less than 78 micrometers |
| At least 40% | less than 74 micrometers |
| At least 30% | less than 69 micrometers |
| At least 20% | less than 65 micrometers |
| At least 10% | less than 59 micrometers |
| At least 5% | less than 54 micrometers |
| At least 1% | less than 46 micrometers |
| Up to 0.5% | less than 44 micrometers |

The molecular sieve catalyst can be a high-resistivity material, i.e., a material having an electrical resistivity greater than 10$^{13}$ ohm-cm, optionally greater than 10$^{14}$ ohm-cm (measured between 100° F. and 200° F.), such as SAPO-containing catalysts. Such materials have a much greater electrical resistivity than zeolite-containing FCC catalysts, which have a resistivity in that temperature range of about 10$^{11}$ ohm-cm. See FIG. 3, which shows the resistivity of the preferred SAPO catalyst. Since the catalyst fines can be fines of un-regenerated catalyst, the resistivity is shown for both carbon-free SAPO catalyst and SAPO catalyst fines having coke deposits thereon.

Selecting a high-resistivity SAPO material as the scouring material can reduce the effectiveness of the electrostatic precipitation of fines, and it can also lead to a greater degree of charging, and, hence, a stronger electrostatic bond to heat transfer surfaces in the reactor effluent and flue gas streams. Consequently, in an embodiment where a SAPO catalyst is used in an oxygenate-to-olefin reaction system, the scouring materials have an electrical resistivity that does not exceed the resistivity of the catalyst. In another embodiment, a scouring material is selected that has an electrical resistivity less than that of the SAPO catalyst. Whether the scouring material has an electrical resistivity greater than, less than, or equal to that of the catalyst, the particles of scouring material are generally selected so that in proximity to the heat transfer surface they have a kinetic energy that is (i) greater than the total binding energy that would otherwise cause the scouring particle to adhere to the heat transfer surface from all forces (e.g., electrostatic forces) and (ii) greater than the foulant's total binding energy.

It is also within the scope of the invention to regulate the kinetic energy of the scoring agent, in proximity to the heat-transfer surface in a range effective for removing foulant from the heat-transfer surface, but without significant fragmentation of the scouring agent and/or foulant. By preventing fragmentation, the number of relatively small (and lower kinetic energy) particles in proximity to the heat transfer surface is not significantly increased, which lessens the likelihood for fouling with the scouring agent. For example, when the scouring agent is a particulate, the kinetic energy of the particles can be regulated by the appropriate selection of the particle's mass and/or relative velocity in proximately to the heat transfer sequence, so that 10% or fewer (or 1% or fewer) of the particles form fragments, based on the total number of particles of scouring agent.

What is claimed is:

1. A fouling mitigation method in an oxygenate to olefin reaction system, the method comprising:
   (a) contacting a feed comprising oxygenate and a catalytically effective amount of an oxygenate conversion catalyst in a reaction zone under catalytic conversion conditions to make a product comprising olefin;
   (b) separating a portion of the catalyst from the product;
   (c) conducting the product to a heat transfer zone comprising at least one heat transfer surface and depositing at least a portion of the catalyst in the product on the heat transfer surface, the catalyst being bound to the heat transfer surface by a total binding energy comprising an electrostatic binding energy; and
   (d) injecting and maintaining at a velocity of about 61 m/s (200 ft/s) in proximity to the heat-transfer surface a scouring agent into the product upstream of the heat transfer surface for removing the deposited catalyst (foulant) wherein the scouring agent has a kinetic energy in proximity to the heat transfer surface greater than the electrostatic binding energy, wherein the agent is glass;
   (e) regenerating a portion of the separated catalyst in a regeneration zone in the presence of an oxygen-containing gas to make an effluent comprising regenerated catalyst and a flue gas;
   (f) separating a portion of the regenerated catalyst from the flue gas and conducting the separated regenerated catalyst to the reaction zone, the regeneration zone, or both;
   (g) conducting the flue gas to a second heat transfer zone comprising at least one heat transfer surface and depositing at least a portion of the regenerated catalyst in the flue gas thereon, the regenerated catalyst being bound to the heat transfer surface of the second heat transfer zone by a second total binding energy comprising a second electrostatic binding energy; and
   (h) injecting a second scouring agent into the flue gas upstream of the second heat transfer zone for removing the deposited regenerated catalyst wherein the second scouring agent has a kinetic energy in proximity to the heat transfer surface of the second heat transfer zone greater than the second electrostatic binding energy, wherein the scouring agent is glass;
   wherein the heat transfer surfaces of the first and second heat transfer zones, respectively, comprises at least one metallic species, and wherein the first and second scouring agents are in particulate form with a size ranging from 1 to 500 micrometers, a density ranging from 0.5 to 4 g/cm$^3$, and an electrical resistivity of $1 \times 10^{15}$ ohm cm or less.

2. The method of claim 1 wherein the feed comprises methanol and the catalyst comprises a molecular sieve having [AlO$_4$], [PO$_4$], and [SiO$_4$] tetrahedral units.

3. The method of claim 1 wherein the catalyst comprises SAPO-34.

4. The method of claim 1 wherein the catalyst has an electrical resistivity greater than $10^{13}$ ohm-cm in a temperature range of about 38° C. to about 93° C.

5. The method of claim 1 wherein the catalyst has an electrical resistivity greater than $10^{14}$ ohm-cm in a temperature range of about 38° C. to about 93° C.

6. The method of claim 1 wherein the catalyst has an electrical resistivity greater than that of zeolite-containing FCC catalyst.

7. The method of claim 1 wherein in proximity to the heat transfer surface the scouring agent particles have a kinetic energy greater than the total binding energy.

* * * * *